United States Patent [19]

Buechel et al.

[11] Patent Number: 4,738,253
[45] Date of Patent: Apr. 19, 1988

[54] GUIDES FOR INCLINED SURGICAL CUTS OR RESECTIONS

[75] Inventors: Frederick F. Buechel, South Orange; Michael J. Pappas, Caldwell, both of N.J.

[73] Assignee: Biomedical Engineering Trust, South Orange, N.J.

[21] Appl. No.: 587,264

[22] Filed: Mar. 7, 1984

Related U.S. Application Data

[63] Continuation-in-part of Ser. No. 336,097, Dec. 31, 1981.

[51] Int. Cl.4 ............................................. A61F 5/04
[52] U.S. Cl. ............................................. 128/92 VW
[58] Field of Search ............... 128/92 H, 303 R, 92 E, 128/92 V, 92 VW, 92 VV, 92 R

[56] References Cited

U.S. PATENT DOCUMENTS

| | | | |
|---|---|---|---|
| 4,457,307 | 7/1984 | Stillwell | 128/92 H |
| 4,474,177 | 10/1984 | Whiteside | 128/92 H |
| 4,487,203 | 12/1984 | Androphy | 128/92 H |
| 4,502,483 | 3/1985 | Lacey | 128/92 H |
| 4,524,766 | 6/1985 | Petersen | 128/92 H |
| 4,574,794 | 3/1986 | Cooke et al. | 128/92 VW |

OTHER PUBLICATIONS

Hungerford et al., "Precise Bone Cuts Every Time . . . ", Howmedica, Rutherford, N.J., 1980.

Primary Examiner—C. Fred Rosenbaum
Assistant Examiner—C. W. Shedd
Attorney, Agent, or Firm—Carella, Byrne, Bain & Gilfillan

[57] ABSTRACT

A guide for a cutting device used to make a surgical cut in a first bone in desired spatial relationship with a pre-existing cut in a second bone is disclosed to include a means for contacting the pre-existing cut to establish a reference for the desired spatial relationship and a body member engaging the means for contacting and including a guide surface for establishing the desired spatial relationship and guiding a surgical cutting tool to cut the first bone in a plane which is not normally inclined with respect to the long axis of the first bone.

14 Claims, 4 Drawing Sheets

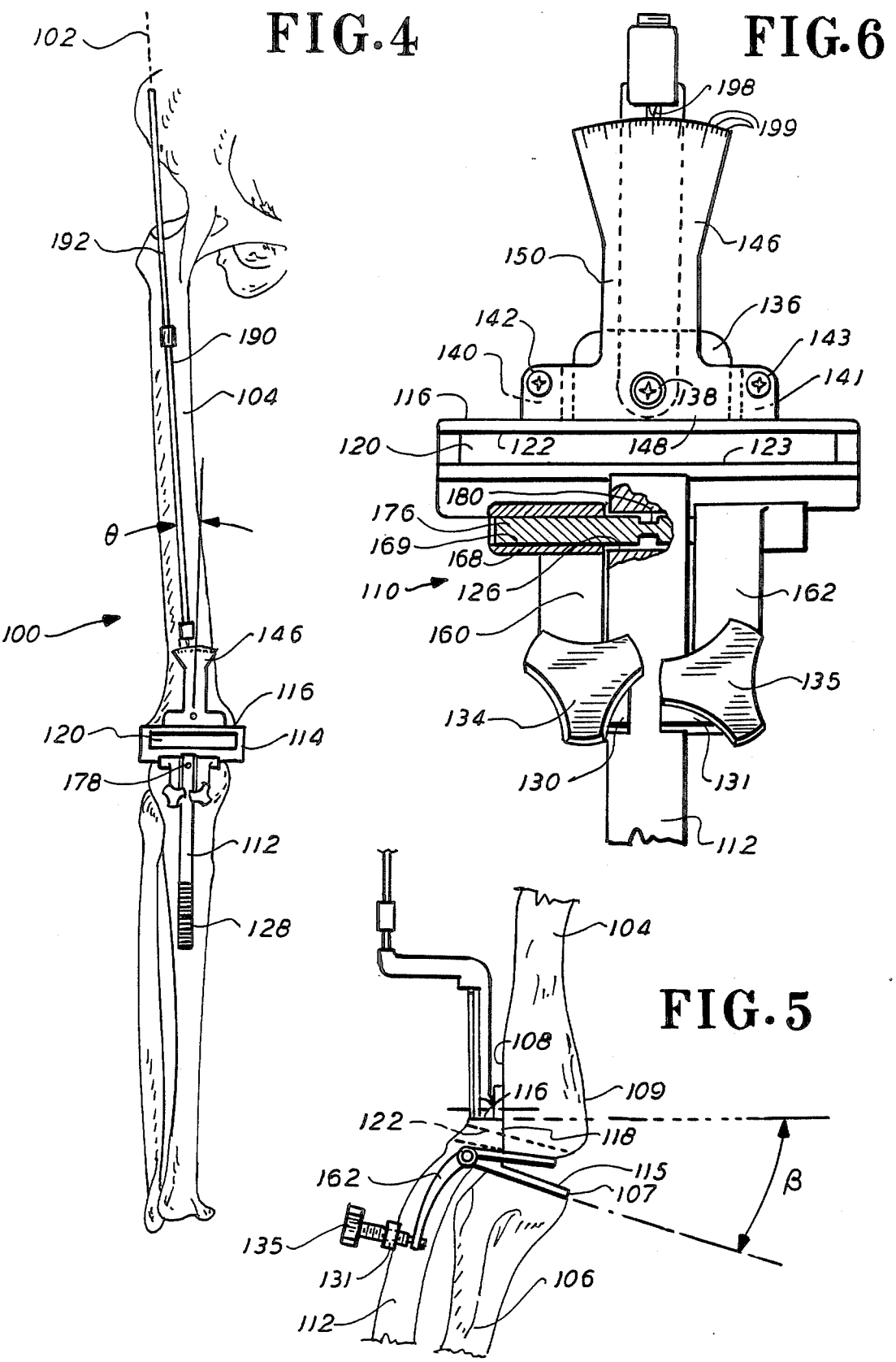

GUIDES FOR INCLINED SURGICAL CUTS OR RESECTIONS

RELATED CASES

This application is a continuation-in-part of our co-pending application Ser. No. 06/336,097 filed Dec. 31, 1981 for GUIDE FOR INCLINED SURGICAL CUTS.

BACKGROUND OF THE INVENTION

1. Field of the Invention

This invention relates to guides for surgical cutting instruments. More specifically, this invention relates to guides for surgical cutting instruments having particular and unique utility for permitting accurately placed cuts or resections in anatomical structure, such as bone, where such cuts or resections are desired to be inclined with respect to some reference plane or line. Such inclined cuts or resections are required, for example, in a surgical procedure for implanting a knee prosthetic joint, where, to minimize shearing forces on the tibial component/tibia interface, the proximal tibial resection plane should be inclined posterialy at approximately 5° to 15° to the general axis of the tibia.

2. Description of the Prior Art

There are many and varied guides which are known in the prior art for producing a cut or resection in an anatomical structure inclined relative to some reference plane or line. However, prior art guides have been found to be inconvenient to use intraoperatively by surgeons thus often resulting in the accuracy of the inclined surgical cut or resection to be less than that desired or required. Further, the prior art is devoid of surgical resection guides which provide for the establishment and maintenance of proper ligamentous tension between joint members during the cutting or resectioning procedures. As a result, resectioning incidental to the preparation of joints for prosthetic implant has been less than satisfactory because of inability to provide for proper ligamentous tension and therewith proper prosthetic placement and operation.

SUMMARY OF THE INVENTION

It is an object of the present invention, therefore, to provide improved guides for surgical cutting, which guides may be more conveniently used by surgeons intraoperatively and which guides more accurately positioned surgical cuts or resections.

An additional object of the present invention is to provide improved guides for surgical cutting, which guides have unique utility for providing guide surfaces for cutting or resectioning on a plane which is inclined with respect to a reference plane or line, particularly where the reference plane or line is a plane or line defined by an axis or surface formed on or defined by an anatomical structure.

Yet another object of the present invention is to provide improved guides for surgical cutting of portions of an anatomical joint wherein the guides provide for establishment of desired ligamentous tension such as to provide resectioned surfaces which support prosthetic components such that when a prosthetic is implanted normal ligamentous tension will be experienced.

It is a further object of the present invention to provide a new and improved guide for producing a femoral resection which is parallel to a previously made inclined tibial resection.

These objects and others not enumerated are achieved by guides for surgical cuts or resections according to the present invention, one embodiment of which may include means for contacting a pre-existing cut on a bone to establish a desired spatial relationship between that bone and an adjacent bone, and a guide engaging the contacting means for guiding a surgical cutting tool during cutting of the second bond. The invention also contemplates an expander associated with the cutting guide, which expander may be used to establish a desired ligamentous tension between the adjacent bones as well as to establish a desired angular relationship between axis of the adjacent bones.

BRIEF DESCRIPTION OF THE DRAWINGS

A more complete understanding of the present invention may be had from the foillowing detailed description thereof, particularly when read in the light of the accompanying drawing wherein:

FIG. 4 is a front or anterior elevational view of a second embodiment of resection guide according to the present invention shown in operating position with respect to a femur and a tibia;

FIG. 5 is a partial side elevational view of the guide of FIG. 4;

FIG. 6 is a front or anterior view, partially in cross-section of the guide of FIG. 4;

DETAILED DESCRIPTION OF THE INVENTION

As set out above, this invention relates to guides for surgical cutting instruments. In particular this invention relates to guides for surgical cutting instruments having particular and unique utility for permitting accurately placed cuts or resections in anatomical structure, such as bone, where such cuts or resections are desired to be inclined with respect to some reference plane or line. The following detailed description of preferred embodiments of the present invention are made in the context of femoral and tibial resectioning incidental to a total knee replacement.

A total knee replacement instrumentation system utilizing among other instruments the improved femoral and tibial resection guides of the present invention, is described in the brochure entitled "N.J. Knee Instrumentation System: Biochemical and Surgical Rationale" by Michael J. Pappas, Ph.D. and Frederick F. Buechel, M.D., published in June 1983 by De Puy Division of Boehringer Manheim Corporation of Warsaw, Ind., by DePuy. This publication is incorporated herein by reference as if fully set forth herein at length.

Figure 1:
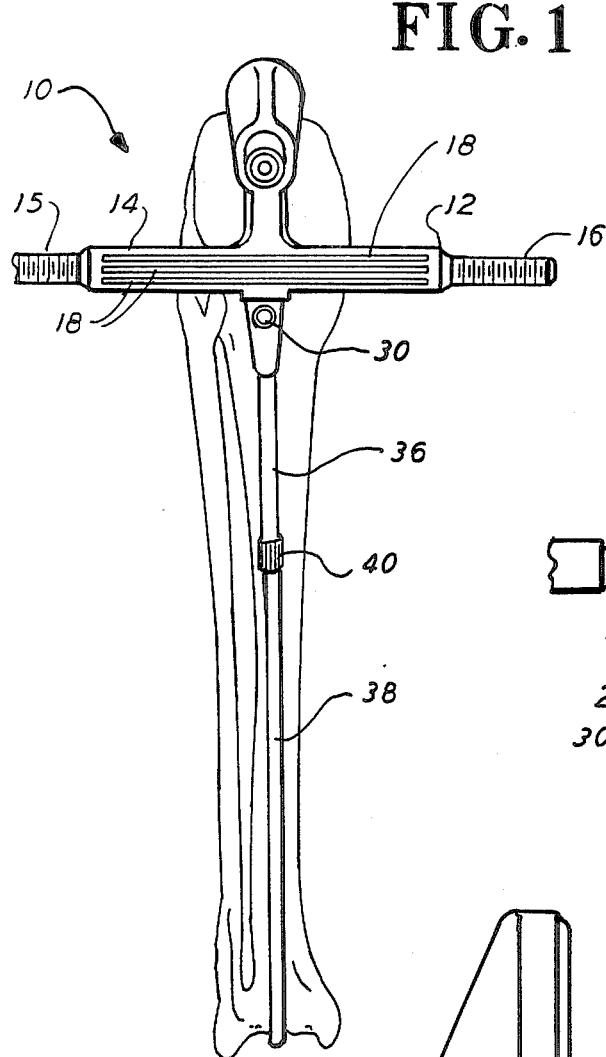
FIG. 1 is a front or anterior elevational view of a tibial resection guide according to the present invention shown in operating position with respect to a femur and a tibia.

Referring therefore to FIG. 1, there is shown a tibial resection guide structured in accordance with the present invention and designated generally by the reference numeral 10. Tibial resection guide 10 includes a body section 12 and an alignment section 17.

Body section 12 is a casting which includes a main body portion 14, a left handle element 15 and a right handle element 16. Disposed through main body portion 14 from left handle element 15 to right handle element 16 are three guide slots 18 defining guide surfaces for cutting devices such as to make tibial resections at various levels. The upper section of body portion 14 is provided with a through-bore 20 the axis of which is in a plane parallel to guide slots 18.

Through bore 20 accommodates the passage therethrough of a positioning rod 22 which is slidably receivable within a bore 24 previously formed in the distal femur 26. In this regard, bore 24 may be formed in accordance with the teaching of our copending application Ser. No. 06/587,264, filed 03/07/84, for POSITIONER FOR SURGICAL INSTRUMENTS.

Figure 2:
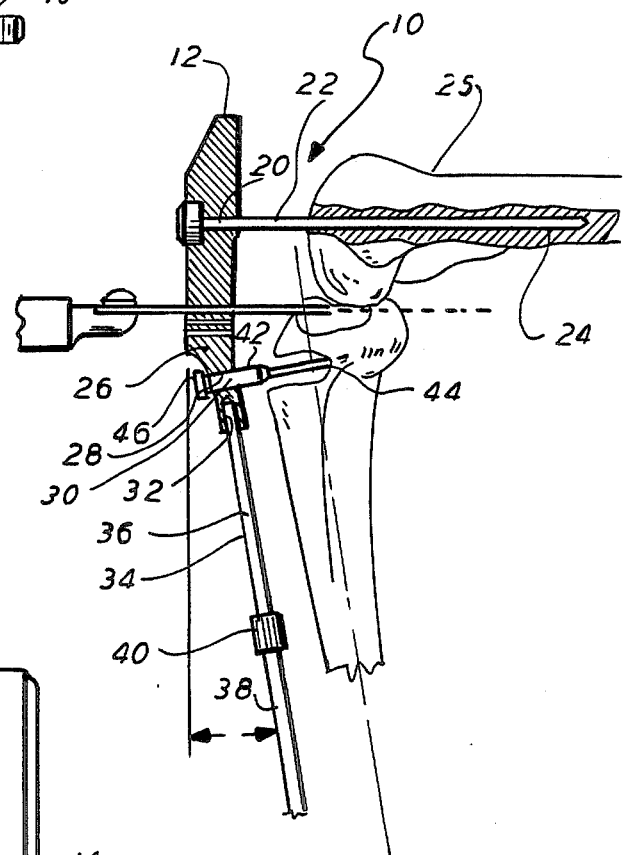
FIG. 2 is a side view of FIG. 1, in partial cross-section.
Figure 3:
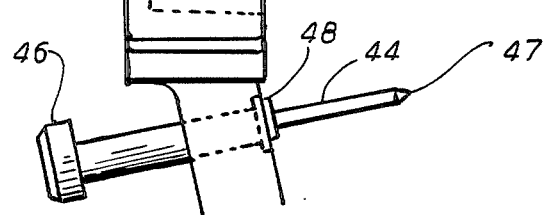
FIG. 3 is an enlarged partial side or lateral view of the tibial resection guide shown in FIGS. 1 and 2.

The lower section 26 of body portion 14 is inclined with respect to the upper section of body 14 at an angle and with respect to the major plane of body 14 as best may be seen in FIG. 2. Lower section 26 is provided with a through bore 28 which accommodates therethrough a fixation pin designated generally by the reference numeral 30. Also formed in the lower section 26 is a bore 32 which extends generally within the inclined plane of lower section 26 and also normal to the axes of guide slots 18.

Disposed within bore 32 is an alignment rod designated generally by the reference numeral 34. Alignment rod 34 includes an upper section 36 which is telescopically received within a lower section 38. The joint between upper section 36 and lower section 38 is provided with a crimping nut 40 which cooperates with longitudinally extending slots formed in the upper end of lower section 38 to provide a deformable friction lock capability of the type which is well known to those having skills in these arts. Thus, the length of alignment rod 34 may be adjusted to accommodate the length of the tibia of the patient being fitted with the prosthesis.

Fixation pin 30 includes a central portion 42 which is sized to be substantially equal in diameter to throughbore 28, a reduced diameter portion 44 at one end and a head 46 at the opposite end. Reduced diameter portion 44 is tapered at its end to define a sharp point 47 to facilitate entry into the proximal tibia in response to the head 46 being struck by the surgeon when the guide 10 is properly positioned as is discussed below. Formed in reduced diameter portion 44 adjacent central portion 42 is an annular groove for receiving a retaining ring 48. In this regard, on assembly the fixation pin 30 without the retaining ring is passed through the throughbore 28 such as to expose the annular channel in reduced diameter portion 44. Retaining ring 48 is then positioned on the pin 30 in the annular channel such as to preclude unintentional removal of the fixation pin from the body. The central portion 42 is dimensioned such that the distance between retaining ring 48 and head 46 is in excess of the length of throughbore 28 by at least an amount sufficient to permit adequate penetration into the proximal tibia to achieve desired fixation. In this regard, it has been found that one inch has been satisfactory for such purposes.

Considering now the use of the tibial resection guide 10 with respect to preparation of a knee joint for total resection, and thus with the joint adequately exposed and bore 24 having been formed in the manner disclosed in our copending application identified above, positioning rod 22 is positioned through the throughbore 20 in body 14 and into bore 24 as best may be seen in FIG. 2. Rod 22 is inserted into bore 24 of the distal femur until alignment rod 34 is positioned adjacent the anterior tibia. The upper and lower sections 36, 38 of alignment rod 34 are then adjusted telescopically until the distal tip of lower section 38 is adjacent the patient's foot (not shown). Thus the amount of extension is dependent upon differences in tibial length as found in different patients. With the rod 34 properly extended, crimping nut 40 is tightened to lock the sections 36, 38 against further telescoping movement during the procedure.

As noted above, the lower section 26 of body portion 14 is inclined at an angle and with respect to the upper section of body 14. This angle, which may be in the range of 5° to 15°, is provided to permit resectioning of the proximal tibial head to result in a surface which is inclined at an angle and downward posteriorly from the horizontal.

To achieve the desired resection inclination, and with the resection guide rotatably positioned with respect to femoral bore 24 an also positioned adjacent the tibia as discussed above, the resection guide 10 is rotatably positioned so as to be in generally parallel alignment with the major longitudinal axis of the tibia when viewed anteriorly as best may be seen in FIG. 1. The tibia is hexed as required to establish substantial parallelism in the sagittal plane between alignment rod 34 and the major longitudinal axis of the tibia as best may be seen in FIG. 2.

With the guide 10 so positioned, the surgeon checks for proper ligamentous tension. Once such proper ligamentous tensiuon is determined or established by other means not part of the present invention, the head of fixation pin 30 is struck with a mallet until the reduced diameter portion 44 is embedded within the proximal tibia, thus being able to retain the tibia in proper position for resectioning.

An appropriate resectioning tool such as a saw blade is then passed through one of the guide slots 18, the particular guide slot being selected by the surgeon based upon the desired amount of resection to be achieved, and the guide slot surface is utilized as the guide surface for cutting the tibia to produce a tibial resection plane 50 at the selected level. The resection plane 50, by reason of the inclination of the lower guide portion as discussed above, is thus provided with a posterior inclination at an angle 10° with respect a plane which is normal to the major longitudinal axis of the tibia. It has been found that such inclination provides a resected surface which is substantially parallel to the general plane of a normal articular surface.

It will be noted by those skilled in these arts that the slidable engagement between body 12 and positioning rod 22 is desirable since the slidable engagement allows positioning of the guide with respect to the tibia with the positioning rod 22 held firmly in the femur. Thus, positioning error resulting from play between the bore 24 in the femur and the positioning rod 22 is not experienced. Further such sliding engagement allows convenient removal of the positioning rod 22 from body 12 thus providing a more favorable configuration of the tibial resection guide for storage.

A second embodiment of a guide for inclined surgical cuts or resections is shown in FIGS. 4 through 10 and designated generally by the reference numeral 100. As was the case with respect to guide 10, guide 100 is particularly useful as a guide for making surgical cuts which are inclined with respect to an axis of a long bone. In this regard, guide 100 is disclosed in use as a distal femoral resection guide with the reference axis being the major longitudinal axis 102 of a femur 104.

The detailed description of this embodiment is made in the context of a total knee replacement procedure as described in the "New Jersey Knee Surgical Procedures Manual" identified above. In this context the proximal tibia 106 has been resected to provide a resection plane 107 inclined with respect to the major longitudinal axis of the tibia. In this regard the procedure for resecting the proximal tibia to achieve such an inclined plane is described above with respect to guide 10. Additionally, the anterior and posterior surfaces 108, 109 of the distal femur have been resected to define flat parallel planes. One procedure for resecting the anterior and posterior distal femur is disclosed in our copending application, for POSITIONER FOR SURGICAL INSTRUMENTS as identified above.

Referring therefore to FIGS. 4 through 10, guide 100 can be seen to include a main body 110 having a handle portion 112, a cutting guide section 114 engaged with, or integral with (as shown) main body 110 and a positioning flange 115 which defines a means for contacting previously resected surface 107. Guide section 114 extends transversely across the anterior distal femur as best may be seen in FIG. 4 and is provided with a flat upper surface 116 and a posterior surface 118 the plane of which is normal to the plane of upper surface 116. Positioning flange 115 extends downwardly posteriorly from the lower edge of posterior surface 118 such that the plane of its lower surface defines an angle B with the plane of flat upper surface 116.

Extending through main body 110 in cutting guide section 114 is a cutting guide slot 120. Guide slot 120 is generally rectangular in cross-section as best may be seen in FIG. 6. Further, the planes of the upper surface 122 and the lower surface 123 of guide slot 120 are parallel to each other and generally parallel to the lower surface of positioning flange 115. Thus any resection accomplished using either of surfaces 122 or 123 as the planar resection guide will result in a resected plane which is parallel to the lower surface of positioning flange 107.

Handle portion 112 which may be unitary with guide section 114, extends generally outwardly and downwardly from cutting guide section 114 as seen in FIG. 4.1 Formed in the upper edge of handle portion 112 is a throughbore 126 the axis of which is generally parallel to the planes upper surface 116 and posterior surface 118. The lower section 128 of handle portion 112 may be provided with knurling or ribbing to facilitate handling by the surgeon. Disposed adjacent the upper end of handle 112 are a first support tab 130 and a second support tab 131. Each of tabs 130, 131 is provided with a threaded throughbore for operatively threadedly receiving therethrough operator screws 134, 135 the details and operation of which are discussed below.

Formed on the upper surface 116 of cutting guide section 114 is a first boss 136. Boss 136 is adjacent the posterior surface 118 of cutting guide section and is generally centrally disposed as seen in FIG. 6. Boss 136 is provided with a throughbore 137 in which is operatively received an axel 138. Also formed on the upper surface 116 of cutting guide section 114 are first and second support bosses 140, 141, respectively. Bosses 140, 141 spaced on either side of the center of cutting guide section 114 and positioned adjacent but slightly spaced from the anterior upper edge of cutting guide section 114. Each of the support bosses 140, 141 is provided with a tapped bore in which is threadedly received screws 142, 143, the function of which is to secure to main body 110 an inclinometer gauge 146.

Inclinometer gauge 146 is provided with a base portion 148 and an upwardly extending portion 150. Formed generally centrally of base portion 148 is a bore in which is operatively received the second end of axel 138. The upper edge of upwardly extending portion 150 is shaped arcuately the radius of curvature being the distance from the axis of axel 138 to the upper edge. Also provided on the surface of upwardly extending portion 150 adjacent the arcuate upper edge are graduations defining 1° increments disposed outwardly on either side of the vertical centerline of upwardly extending portion 150. Also formed in the base portion 148 of gauge 146 are a pair of throughbores which are spaced such as to correspond in position to the tapped bores of bosses 140, 141. The throughbores in base portion 148 accommodate the passage therethrough of screws 142, 143 such to rigidly secure inclinometer gauge 146 to main body 110. In this regard it should be noted that when the inclinometer gauge 146 is assembled to main body 110, the line extending along the surface of gauge 146 from the center or zero inclinometer position through the axis of axel 38 is perpendicular to the anterior edge of upper guide surface 122 of cutting guide section 114.

Figure 7:
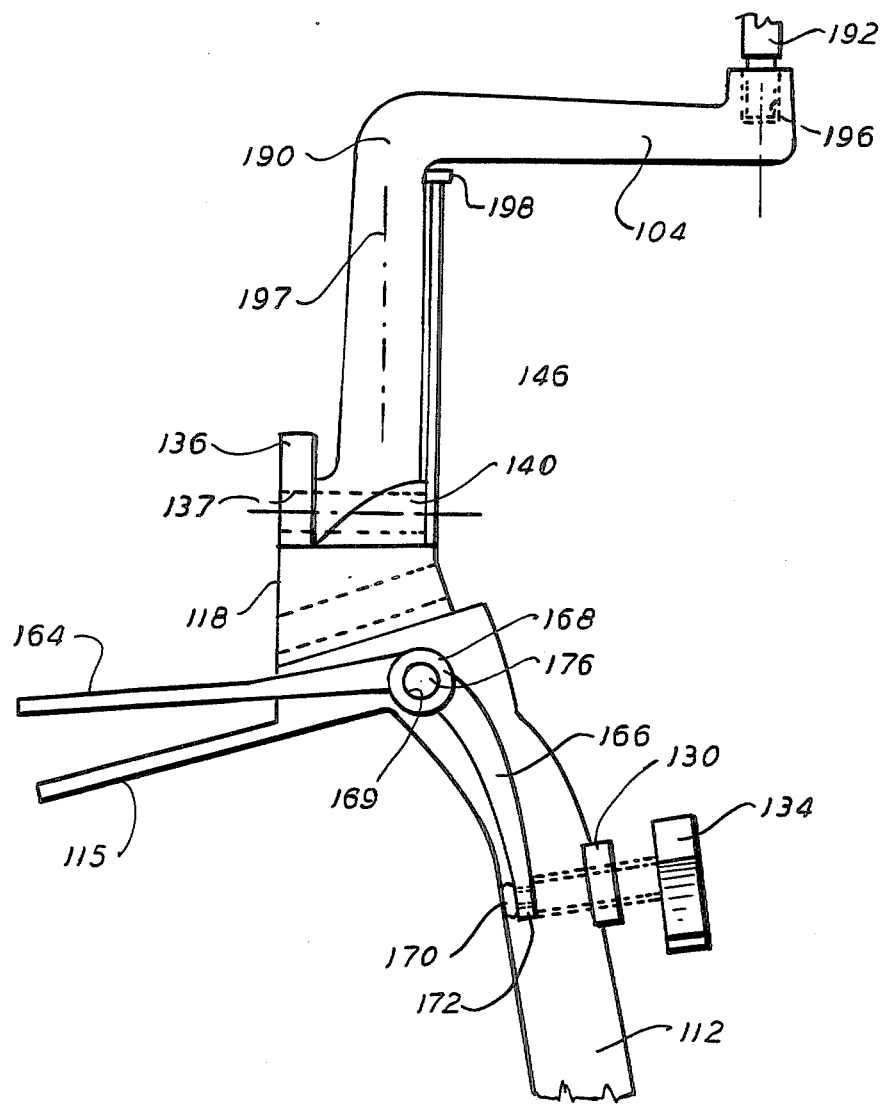
FIG. 7 is a side view through the plane 7—7 of FIG. 6.

Referring now to FIGS. 6 and 7, there is shown expander means for separating the distal femur from the proximal tibia such that proper ligamentous tension may be established during resectioning whereby to provide resected surfaces which, when provided with the prosthetic replacement, will be oriented such that proper ligamentous tension is established.

Thus, as best may be seen from FIG. 6, the guide 100 is provided with a left expander clement 160 and a right expander element 162. In this regard, expander element 160 and 162 are identical in structure except that one is the opposite hand, i.e. the mirror image of the other. Accordingly only one of the expander elements will be discussed in detail, it being understood that the description is equally appropriate for the other.

Referring, therefore, to expander element 160, the element can be seen to be a pivoted level including a distractor plate 164, an actuator arm 166, a boss 168 through which is provided a throughbore 169. Formed in the distal end of actuator arm 166 is a slot 170. Slot 170 is provided to receive rotatably therein an annular channel 172 formed adjacent the internal end of operator screw 134. Thus it can be seen that rotation of operator screw 134, which is threadedly engaged through first support tab 130, causes the anterior or posterior displacement of operator screw 134 and therewith the distal end of actuator arm 166.

Extending through bore 169 of boss 168, through bore 126 in handle portion 112 and also through the corresponding bore formed in the boss 174 of right expander element 162 is an expander axel 176. Axel 176 rotatably supports expander elements 160, 162 with respect to handle portion 112. The axel 176 is retained within bore 126 of handle portion 112 by a set screw 178 (FIG. 7) which is threadedly received within a tapped bore formed in handle portion 112. Set screw 178 may be rotatably advanced into handle portion 112 such as to extend into an annular channel 180 formed generally centrally of axel 176. Conversely, set screw may be rotatably withdrawn from extension into bore 126 of handle portion 112 such as to permit axel 176 to be longitudinally axially displaced from bore 126 thereby permitting disassembly of expander elements 160, 162 form handle portion 112.

As best may be seen in FIG. 7, displacement of the distal end of actuator arm 166 in response to the rotation of operator screw 134 causes a rotation of the expander element about the axis of axel 176. Clockwise rotation of element 160 causes a further angular separation between positioning flange 115 and distractor plate 164. Conversely, counter-clockwise rotation of element 160 about axel 176 causes a reduction in the angle between positioning flange 115 and distractor plate 164. It should also be noted that in addiution to providing the operative connection between operator screw 134 and expander element 160, the cooperation between slot 170 in the distal end of actuator arm 166 and the channel 172 in operator screw 134 seem to retain expander element on axel 176 by precluding relative longitudinally axial movement between box 168 and axel 176.

Pivotally mounted on axel 138 is alighment rod 190. Alignment rod 190 includes a rod 192 which is threadedly received in a pivot arm 194. The distal end of pivot arm 194 is provided with a throughbore 195 through which receives axel 138. The proximal end of pivot arm 194 is provided with a threaded bore 196 for receiving alignment rod 190. The axis of bore 196 is generally parallel to but displaced from the major vertically extending axes 197 of the distal end of pivot arm 194 by an amount sufficient to insure that extendable rod 192 may be pivoted without interference from the patient's anatomy. In this regard, the pivoting of arm 194 is detentable in one degree increments through the cooperation of a spring element 198 which is secured to the anterior surface of pivot arm 194 and which cooperates with grooves formed in the upper arcuately shaped edge of inclinometer gauge 146 at points corresponding to the one degree graduations formed on the surface of upwardly extending portion 150 of inclinometer gauge 146.

Considering now the use of resecting guide 100 in the context of resecting a distal femur on a plane having a desired predetermined relationship with a previously resected surface on a proximal tibia, and with particular reference to FIGS. 4 and 5, the lower or inferior flat surface of positioning flange 155 is placed in surface to surface contact with the previously resected surface 107 of tibia 106 after rotating screws 135 and 134 until the distractor plate 164 of expander element 160 lays on the upper surface of the positioning flange 115. Alignment rod 192 is then pivotally positioned to an angle as shown on inclinometer gauge 146, which angle corresponds to the proper valgus inclination for the patient as determined by the surgeon. Angle can vary between approximately four degrees and twelve degrees to accommodate the particular characteristics of a patient's anatomy.

With alignment rod 190 so prepositioned operating screws 134 and 135 are rotated by the surgeon to rotate extender elements 160 and 162 such as to establish the desired degree of ligamentous tension across the joint while simultaneously changing the valgus angle of the tibia such that the axis of alignment rod 190 is generally parallel to the longitudinal major axis 102 of femur 104 or is directed toward anterior-superior spine of the Illiac crest. More specifically, as best may be seen in FIG. 5, manipulation of operating screw 135 in a clockwise direction causes advancement of the screw through support tab 131 and a counter-clockwise rotation of direction, its distractor plate displaces the femur upwardly with respect to the tibia thus increasing ligamatous tension. The use of two independently operated extenders 160, 162 permits substantially independent tensioning of the medial and lateral collateral ligaments and maintenance of the proper valgus angle between the femur and the tibia.

As best may be seen in FIG. 5, continued clockwise rotation of extender element 160 causes an increase in the angle between the planes of positioning flange 115 and distractor plate 164. Because these planes are not parallel the forces generated between the surfaces of flange 115 and the proximal tibia, and between distractor plate 164 and the distal femur generate a resultant force which tends to hold the posterior surface 118 of guide section 114 firmly against the previously resected anterior surface 108 of femur 104. Such surface-to-surface engagement effects a self-alignment of the resection guide with respect to angular orientation as to the distal femur.

With the joint so oriented and with the ligamatous tension so adjusted, the surgeon may release the instrument which will maintain the desired orientation and tension. At this point the resection of the distal femur may be made.

The distal femoral resection is made by placing a saw blade (not shown) against the upper surface 122 of guide slot 120. In this regard, use of the upper surface 122 as the guide surface for resectioning eliminates the thickness of the saw blade as a potential for error in location of the resection plane.

Figure 8:
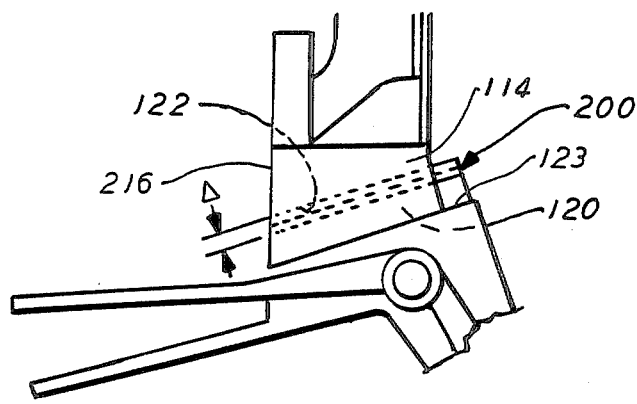
FIG. 8 is a side view of the guide of FIG. 4 showing use of guide surface adapter.

It should also be noted that the location of the cutting guide surface in guide slot 120 may be varied from the largest offset is between surface 107 and the resection plane of the distal femur, the situation shown in FIG. 8, to a smaller degree of offset through the use of a guide adaptor which is removably insertable in guide slot 120.

Figure 9:
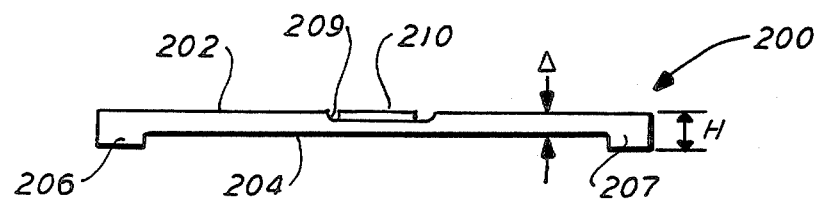
FIG. 9 is a front elevational view of the guide surface adapter shown in FIG. 8.
Figure 10:
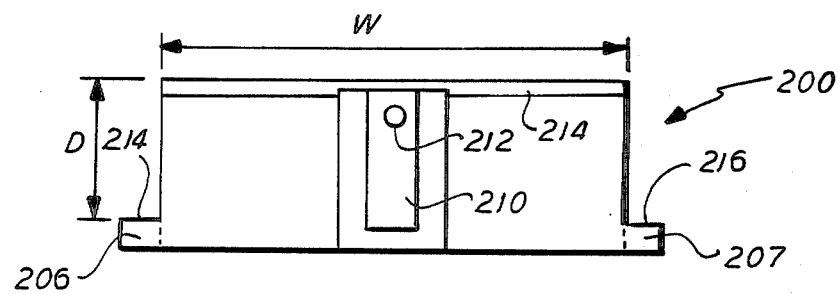
FIG. 10 is a plan view of the adapter of FIG. 9.

Referring therefore to FIGS. 8, 9 and 10, a guide surface adaptor is shown and designated generally by the reference numeral 200. Adaptor is shown in FIG. 8 to be disposed within guide slot 120 of the guide section 114 of guide 100 as disclosed in detail above.

Adaptor 200 is a generally rectangular structure having an upper surface 202, a lower surface 204 and a pair of tabs 206, 207 formed at the anterior edges of the structure. Formed in the upper surface 202 of adaptor 200 is a shallow channel 209. Mounted in channel 209 is a thin leaf spring element 210 which is secured within channel 209 by a rivet 212.

The posterior edge 214 of adaptor 200 is beveled such as to provide a surface which will be coplanar with the posterior surface 216 of guide section 114 when the adapter is inserted in guide slot 120. In the regard, adaptor 200 is dimensioned such that its width W (FIG. 10) is substantially equal to the width of guide slot 120 and its depth D is substantially equal to the depth of guide slot 120. The height H (FIG. 9) of tabs 206, 207 is substantially equal to the normal distance between upper surface 122 and lower surface 123 of guide slot 120. The thickness of adaptor 200, i.e. the normal spacing between the planes of upper and lower surfaces 202, 204 defines the distance by which the adjusted cutting guide surface 204 is displace from the original cutting guide surface 122. As will be recognized by those skilled in these acts, a plurality of adaptors having differing dimensions for may be provided to permit a surgeon a wide range of possible relationships between the reference plane 107 of a resected tibia and a desired resected plane of a distal femur.

In utilizing the adaptor 200, an adaptor having the desired dimension is chosen by the surgeon and inserted, into guide slot 120 until the posterir surfaces 214, 216 of tabs 206 and 207 respectively engage the anterior surface of guide section 114. Insertion of adapter 200 into guide slot 120 causes leaf spring 210 to engage and be slightly deflected by the upper surface 122 of slot 120. Such deflection generates a slight friction force between the spring and surface 122 to preclude the adaptor from unintentional removal from slot 120. With the adaptor so inserted, the surgeon may use surface 204 as the resecting guide surface. Since surface 204 is, as is upper surface 122 of guide slot 120, essentially an extension of the surface to be resected the thickness of the saw blade will not affect the location of the resection plane. This would not be the case if one were to position the lower surface 123 of guide slot 120 for the purposes of providing a guide for resection of the distal femur. Here the resection plane would be offset from said lower surface by the thickness of the balde.

It can be seen, therefore, that the embodiment of the present invention as disclosed in detail above, define guides for surgical cuts or resections which are unique and of particular utility with respect to tibial and femoral resections. It will also be recognized by those skilled in these arts that many modifications and variations may be mde to the structure of the disclosed embodiments without departing from the spirit of the present invention.

We claim:

1. A guide for a cutting device used to make a surgical cut in a first bone in desired spatial relationship with a pre-existing cut in a second bone, said first bone having a long axis and an articular surface adjacent the portion of the bone to be cut, said guide comprising:
    means for contacting said pre-existing cut to establish a reference for said desired spatial relationship; and
    body means engaging said means for contacting, said body means including a guide surface displaced from said means for contacting by an amount defining said desired spatial relationship, said guide surface for engaging a surgical cutting tool during cutting of said first bone, said body means further including means for maintaining said first bone in a position with respect to said second bone such that said guide surface is within a plane which is inclined from but not perpendicular to the long axis of said first bone and also generally parallel to the general plane of said articular surface prior to being cut.

2. A guide according to claim 1 wherein said pre-existing cut in said second bone is a bore and said means for contacting said pre-existing cut comprises a rod slidably received within said bore.

3. A guide according to claim 1 wherein said pre-existing cut in said second bone is a resected surface and said means for contacting comprises a plate for engaging at least a portion of said resected surface.

4. A guide according to claim 3 wherein said resected surface is generally planar, said plate for engaging at least a portion of said resected surface has a planar surface for engaging said resected surface, and wherein said guide surface is generally parallel to said planar surface of said plate.

5. A guide according to claim 1 wherein said second bone has a long axis, and wherein said reference for said desired spatial relationship is in a plane which s inclined with respect to the long axis of said second bone such as to be not normal to said long axis of said second bone.

6. A guide according to claim 5 wherein said guide surface is in a plane which is parallel to a plane containing said reference.

7. A guide according to claim 1 including means on said body means for selectively varying the desired spatial relationship.

8. A guide according to claim 7 wherein said guide surface is defined by a slot formed in said body means, and said means for selectively varying the desired spatial relationship comprises a plate means removably received within said slot.

9. A guide according to claim 1 wherein said first bone and said second bone ware connected by ligametns, and further including means for establishing a desired degree of ligamentous tension during cutting of said first bone.

10. A guide according to claim 9 wherein aid means for establishing a desired degree of ligamentous tension comprises at least one expander means positionable between said first and second bones, said expander means including a first element for bearing against said first bone, a second element for bearing against said secondb one, and means engaging said first and second elements for selectively increasing or decreasing the space between said first and second elements whereby to change the spacing between said first and secondb ones and therewith the ligamentous tension therebetween.

11. A guide according to claim 10 wherein said second element is said means for contacting said pre-existing cut.

12. A guide according to claim 10 wherein said second element is rotatably mounted on said body means.

13. A guide according to claim 1 wherein said first bone is a tibia and said second bone is a femur and wherein said means for contacting said pre-existing cut comprises a positioning rod disposed on said body means, said guide surface being parallel to the axis of said positioning rod and further being either a plane inclined with respect to the long axis of said tibia by an angle of between 5° and 15°.

14. A guide according to claim 1 wherein said first bone is a femur and said second bone is a tibia, and wherein said means for contacting said pre-existing cut comprises of a planer surface disposed on said body means, said guide surface being parallel to said planar surface and further being within a plane inclined with respect to the long axis of said tibia by an angle of between 5° and 15°.

* * * * *